United States Patent
Lee et al.

(10) Patent No.: US 9,896,465 B2
(45) Date of Patent: Feb. 20, 2018

(54) PHOSPHONIUM COMPOUND, PREPARATION METHOD THEREOF, EPOXY RESIN COMPOSITION INCLUDING THE SAME, AND SEMICONDUCTOR DEVICE PREPARED BY USING THE SAME

(71) Applicant: SAMSUNG SDI CO., LTD., Yongin-si, Gyeonggi-do (KR)

(72) Inventors: Dong Hwan Lee, Suwon-si (KR); Min Gyum Kim, Suwon-si (KR); So Yoon Kim, Suwon-si (KR); Woo Chul Na, Suwon-si (KR); Yoon Man Lee, Suwon-si (KR); Ji Yoon Cho, Suwon-si (KR); Ki Hyeok Kwon, Suwon-si (KR); KyoungChul Bae, Suwon-si (KR); Eun Jung Lee, Suwon-si (KR); Joo Young Chung, Suwon-si (KR); Jin Min Cheon, Suwon-si (KR); Jin Woo Choi, Suwon-si (KR); Seung Han, Suwon-si (KR)

(73) Assignee: SAMSUNG SDI CO., LTD., Yongin-Si, Gyeonggi-Do (KR)

( * ) Notice: Subject to any disclaimer, the term of this patent is extended or adjusted under 35 U.S.C. 154(b) by 0 days.

(21) Appl. No.: 15/189,057

(22) Filed: Jun. 22, 2016

(65) Prior Publication Data
US 2016/0368937 A1 Dec. 22, 2016

(30) Foreign Application Priority Data
Jun. 22, 2015 (KR) .................. 10-2015-0088742

(51) Int. Cl.
*C08L 63/00* (2006.01)
*C07C 233/00* (2006.01)
(Continued)

(52) U.S. Cl.
CPC .......... *C07F 9/5442* (2013.01); *C07C 235/64* (2013.01); *C08G 59/621* (2013.01);
(Continued)

(58) Field of Classification Search
CPC ... C07F 9/5442; C09D 163/00; H01L 23/295; H01L 24/16; H01L 24/29; H01L 24/32;
(Continued)

(56) References Cited

FOREIGN PATENT DOCUMENTS

| JP | 2013-166959 A | 8/2013 |
|---|---|---|
| KR | 10-2015-0042087 A | 4/2015 |

OTHER PUBLICATIONS

Apostolopoulou et al., "Oxidovanadium(IV/V) Complexes as New Redox Mediators in Dye-Sensitized Solar Cells: A Combined Experimental and Theoretical Study", Inorganic Chemistry, Inorganic Chemistry, Apr. 6, 2015, vol. 54, p. 3979-3988.*
(Continued)

*Primary Examiner* — David Karst
(74) *Attorney, Agent, or Firm* — Lee & Morse, P.C.

(57) ABSTRACT

A phosphonium compound, a method of preparing the same, an epoxy resin composition including the same, and a semiconductor device encapsulated with the same, the compound being represented by Formula 1:

Formula 1

(Continued)

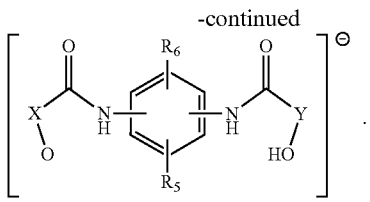

14 Claims, 1 Drawing Sheet

(51) Int. Cl.
| | |
|---|---|
| *C07C 235/00* | (2006.01) |
| *C07C 237/00* | (2006.01) |
| *C07F 9/02* | (2006.01) |
| *C07F 9/54* | (2006.01) |
| *C09D 163/00* | (2006.01) |
| *H01L 23/29* | (2006.01) |
| *C07C 235/64* | (2006.01) |
| *C08G 59/62* | (2006.01) |
| *C08G 59/68* | (2006.01) |
| *H01L 23/00* | (2006.01) |

(52) U.S. Cl.
CPC ......... *C08G 59/688* (2013.01); *C09D 163/00* (2013.01); *H01L 23/295* (2013.01); *H01L 24/16* (2013.01); *H01L 24/29* (2013.01); *H01L 24/32* (2013.01); *H01L 24/73* (2013.01); *H01L 24/92* (2013.01); *H01L 2224/16227* (2013.01); *H01L 2224/16245* (2013.01); *H01L 2224/2929* (2013.01); *H01L 2224/32225* (2013.01); *H01L 2224/32245* (2013.01); *H01L 2224/73204* (2013.01); *H01L 2224/92125* (2013.01); *H01L 2924/18161* (2013.01); *H01L 2924/3512* (2013.01)

(58) Field of Classification Search
CPC ................... H01L 24/73; H01L 24/92; H01L 2224/16227; H01L 2224/16245; H01L 2224/2929; H01L 2224/32225; H01L 2224/32245; H01L 2224/73204; H01L 2224/92125; H01L 2924/18161; H01L 2924/3512; C07C 235/64; C08G 59/621; C08G 59/688
USPC ............................... 564/123; 568/9; 523/400
See application file for complete search history.

(56) References Cited

OTHER PUBLICATIONS

Provisional double patenting rejection over claims of the above-identified application; USPTO Office action dated Feb. 24, 2017, in U.S. Appl. No. 14/918,916.
Korean Office Action dated May 26, 2017 for corresponding Korean Patent Application No. 10-2015-0088742.

\* cited by examiner

PHOSPHONIUM COMPOUND, PREPARATION METHOD THEREOF, EPOXY RESIN COMPOSITION INCLUDING THE SAME, AND SEMICONDUCTOR DEVICE PREPARED BY USING THE SAME

CROSS-REFERENCE TO RELATED APPLICATION

Korean Patent Application No. 10-2015-0088742, filed on Jun. 22, 2015, in the Korean Intellectual Property Office, and entitled: "Phosphonium Compound, Preparation Method Thereof, Epoxy Resin Composition Comprising the Same and Semiconductor Device Prepared by Using the Same," is incorporated by reference herein in its entirety.

BACKGROUND

1. Field

Embodiments relate to a phosphonium compound, a method of preparing the same, an epoxy resin composition including the same, and a semiconductor device prepared using the same.

2. Description of the Related Art

Transfer molding is widely used as a method of packaging semiconductor devices, such as integrated circuits (ICs) and large scale integration (LSI) chips, with epoxy resin compositions to obtain semiconductor devices due to its advantages of low cost and suitability for mass production. In transfer molding, modification of epoxy resins or phenol resins as curing agents may lead to an improvement in characteristics and reliability of semiconductor devices.

Epoxy resin compositions may include an epoxy resin, a curing agent, a curing catalyst, and the like. As the curing catalyst, imidazole catalysts, amine catalysts, and phosphine catalysts may be used.

SUMMARY

Embodiments are directed to a phosphonium compound, a method of preparing the same, an epoxy resin composition including the same, and a semiconductor device prepared using the same.

The embodiments may be realized by providing a phosphonium compound represented by Formula 1:

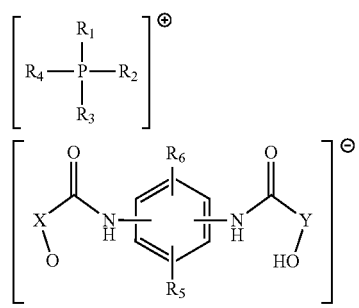

Formula 1 wherein: $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom; X and Y are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ and $R_6$ are each independently hydrogen, a hydroxyl group, a $C_1$ to $C_{20}$ alkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group.

$R_1$, $R_2$, $R_3$, and $R_4$ may each be independently a substituted or unsubstituted $C_6$ to $C_{30}$ aryl group.

At least one of $R_1$, $R_2$, $R_3$, and $R_4$ may be a hydroxyl group-substituted $C_6$ to $C_{30}$ aryl group.

The phosphonium compound may be represented by one of the following Formulae 1a to 1h.

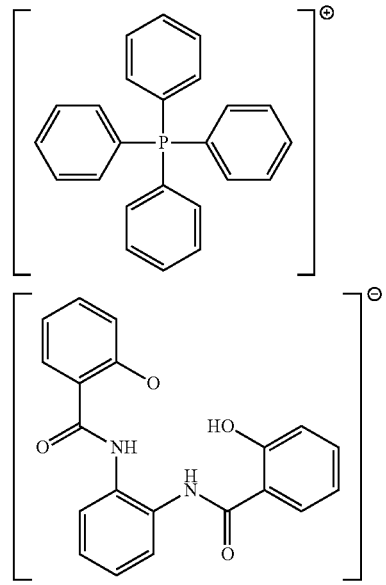

Formula 1a

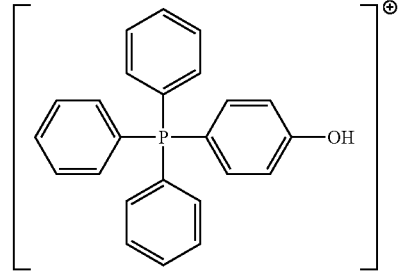

Formula 1b

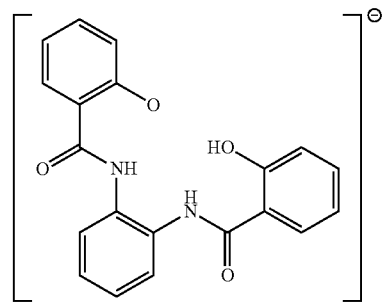

-continued
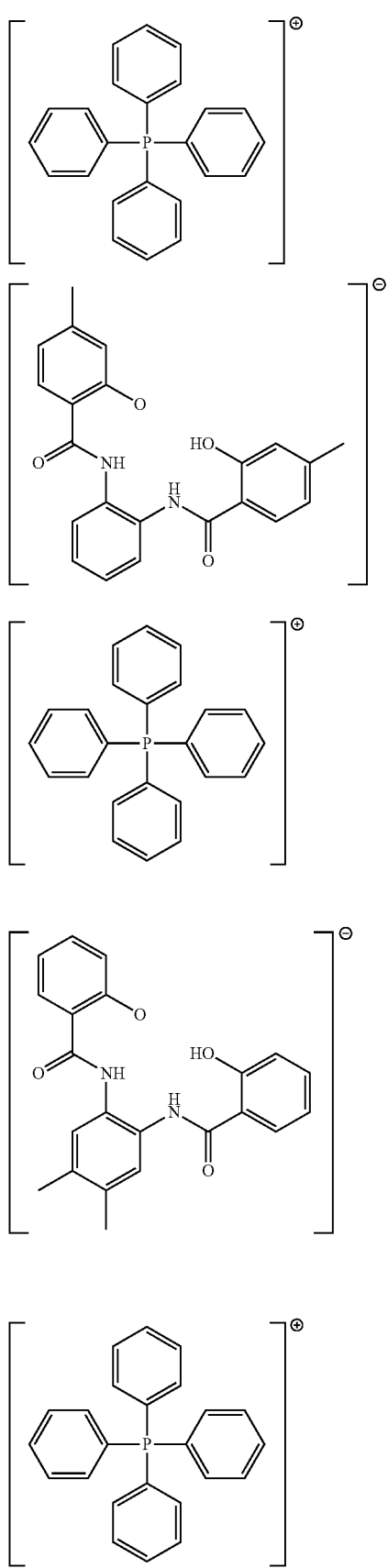
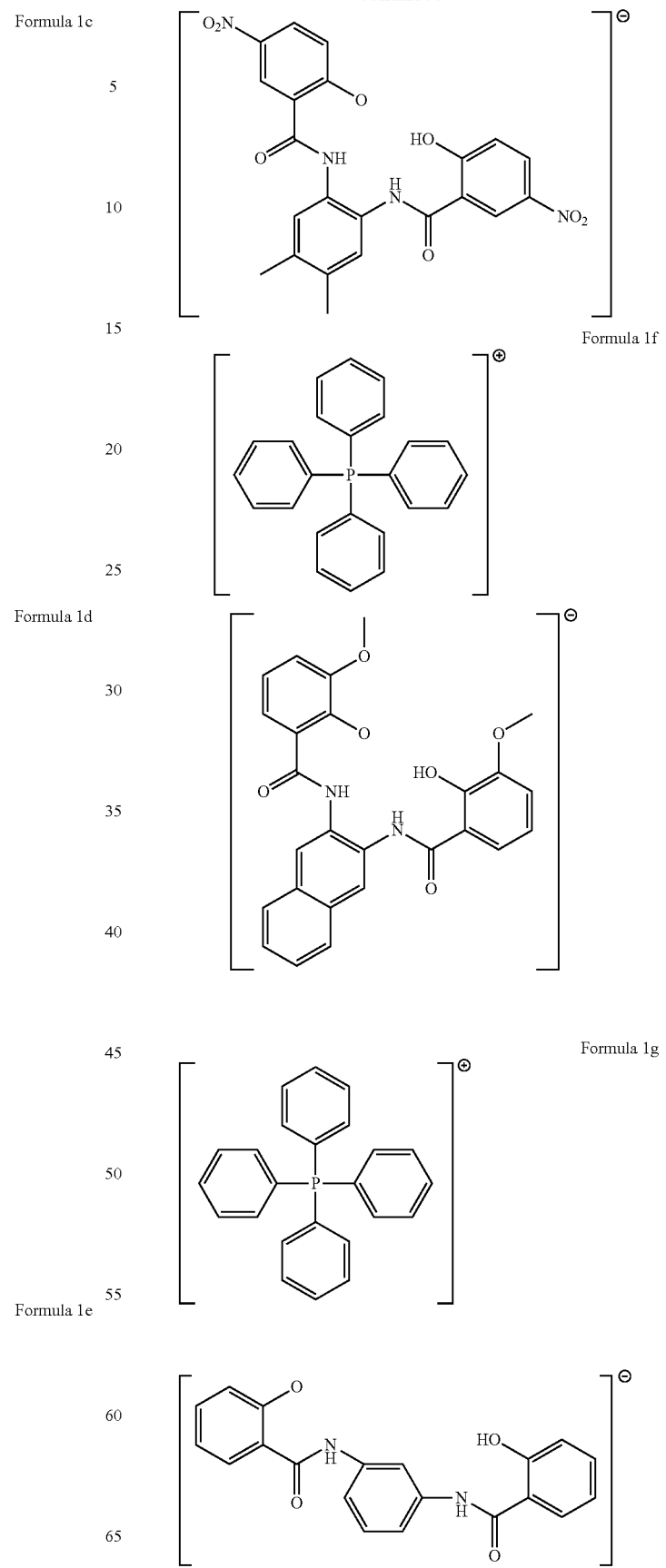
Formula 1c
Formula 1d
Formula 1e
Formula 1f
Formula 1g Formula 1h

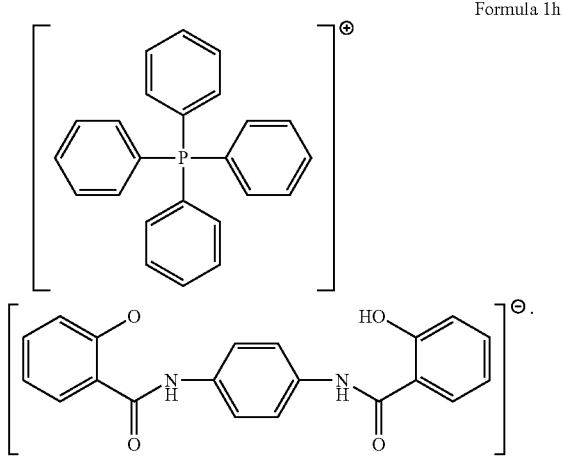

The embodiments may be realized by providing a method of preparing a phosphonium compound, the method comprising reacting a phosphonium cation-containing compound represented by Formula 2 with a phenylene-bis-benzamide anion-containing compound represented by Formula 3:

Formula 2

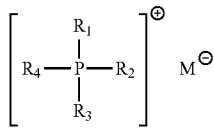

Formula 3

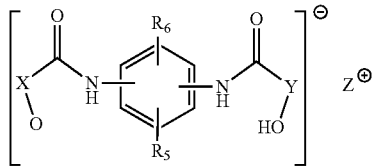

wherein, in Formula 2, $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom, and M is a halogen, and wherein, in Formula 3, X and Y are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ and $R_6$ are each independently hydrogen, a hydroxyl group, a $C_1$ to $C_{20}$ alkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group; and Z is an alkali metal or Ag.

The embodiments may be realized by providing an epoxy resin composition including an epoxy resin, a curing agent, an inorganic filler, and a curing catalyst, wherein the curing catalyst includes the phosphonium compound according to an embodiment.

The epoxy resin may include at least one of a bisphenol A epoxy resin, a bisphenol F epoxy resin, a phenol novolac epoxy resin, a tert-butyl catechol epoxy resin, a naphthalene epoxy resin, a glycidylamine epoxy resin, a cresol novolac epoxy resin, a biphenyl epoxy resin, a linear aliphatic epoxy resin, a cycloaliphatic epoxy resin, a heterocyclic epoxy resin, a Spiro ring-containing epoxy resin, a cyclohexane dimethanol epoxy resin, a trimethylol epoxy resin, and a halogenated epoxy resin.

The curing agent may include a phenol resin.

The curing agent may include at least one of a phenol aralkyl phenol resin, a phenol novolac phenol resin, a xyloc phenol resin, a cresol novolac phenol resin, a naphthol phenol resin, a terpene phenol resin, a polyfunctional phenol resin, a dicyclopentadiene-based phenol resin, a novolac phenol resin synthesized from bisphenol A and resorcinol, a polyhydric phenolic compound, an acid anhydride, and an aromatic amine.

The curing catalyst may be present in the epoxy resin composition in an amount of about 0.01 wt % to about 5 wt %, in terms of solid content.

The phosphonium compound may be present in the curing catalyst in an amount of about 10 wt % to about 100 wt %, based on a total weight of the curing catalyst.

The epoxy resin composition may have a curing shrinkage rate of less than about 0.40%, as calculated according to Equation 1:

$$\text{Curing shrinkage} = (|C-D|/C) \times 100 \qquad \text{Equation 1}$$

wherein, in Equation 1, C is a length of a specimen obtained by transfer molding the epoxy resin composition at 175° C. under a load of 70 kgf/cm$^2$, and D is a length of the specimen after post-curing the specimen at 170° C. to 180° C. for 4 hours and cooling.

The epoxy resin composition may have a storage stability after 72 hours of about 85% or more, as calculated according to Equation 2:

$$\text{Storage stability} = (F1/F0) \times 100 \qquad \text{Equation 2}$$

wherein, in Equation 2, F1 is a flow length in inches of the epoxy resin composition, measured after storing the composition at 25° C./50% RH for 72 hours, using a transfer molding press at 175° C. and 70 kgf/cm$^2$ in accordance with EMMI-1-66, and F0 is an initial flow length in inches of the epoxy resin composition.

The embodiments may be realized by providing a semiconductor device encapsulated with the epoxy resin composition according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
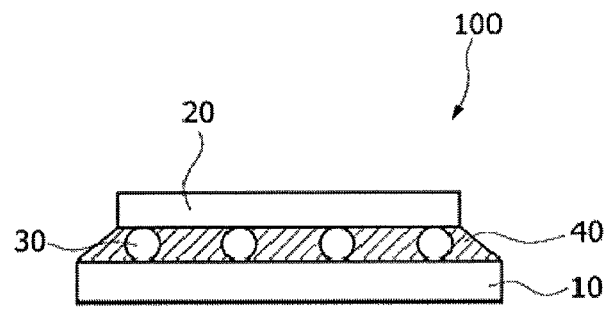
FIG. 1 illustrates a cross-sectional view of a semiconductor device according to one embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. Like reference numerals refer to like elements throughout.

As used herein, the term "substituted" in "substituted or unsubstituted" means that at least one hydrogen atom in the corresponding functional group is substituted with a hydroxyl group, a halogen atom, an amino group, a nitro group, a cyano group, a $C_1$ to $C_{20}$ alkyl group, a $C_1$ to $C_{20}$ haloalkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group. The term "halo" means fluorine, chlorine, iodine or bromine.

As used herein, the term "aryl group" refers to a substituent in which all elements in the cyclic substituent have p-orbitals and the p-orbitals form a conjugated system. Aryl groups include mono- or fused-functional groups (namely, rings of carbon atoms which share adjacent electron pairs). The term "unsubstituted aryl group" refers to a monocyclic or fused polycyclic $C_6$ to $C_{30}$ aryl group. Examples of unsubstituted aryl groups may include phenyl groups, biphenyl groups, naphthyl groups, naphthol groups, and anthracenyl groups, without being limited thereto.

As used herein, the term "heteroaryl group" means a $C_6$ to $C_{30}$ aryl group in which a ring comprises carbon atoms and 1 to 3 heteroatoms selected from nitrogen, oxygen, sulfur and phosphorus. Examples of heteroaryl groups may include, but are not limited to, pyridinyl, pyrazinyl, pyrimidyl, pyridazinyl, triazinyl, quinolinyl, isoquinolinyl, quinoxalinyl, acridinyl, quinazolinyl, cinnolinyl, phthalazinyl, thiazolyl, benzothiazolyl, isoxazolyl, benzisoxazolyl, oxazolyl, benzoxazolyl, pyrazolyl, indazolyl, imidazolyl, benzimidazolyl, purinyl, thiophenyl, benzothiophenyl, furanyl, benzofuranyl, and isobenzofuranyl.

As used herein, the term "hetero" in "heterocycloalkyl group", "heteroaryl group", "heterocycloalkylene group", and "heteroaryllene group" refers to an atom selected from nitrogen, oxygen, sulfur, or phosphorus.

According to an embodiment, a phosphonium compound may include, e.g., a phosphonium cation and an anion having a hydroxyl group and an amide group at the same time. In an implementation, the phosphonium compound may be represented by the following Formula 1.

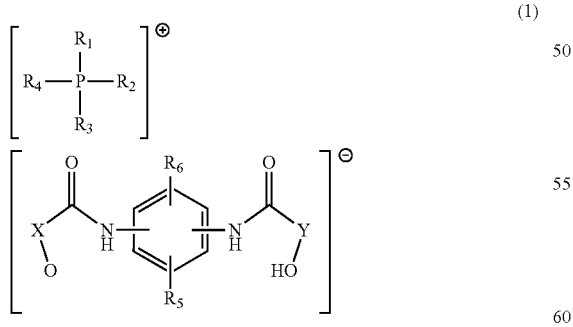
(1)

In Formula 1, $R_1$, $R_2$, $R_3$, and $R_4$ may each independently be or include, e.g., a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom. X and Y may each independently be or include, e.g., a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group. $R_5$ and $R_6$ may each independently be, e.g., hydrogen, a hydroxyl group, a $C_1$ to $C_{20}$ alkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group. In an implementation, $R_5$ and $R_6$ may each independently be or include, e.g., hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group.

In an implementation, in Formula 1, $R_1$, $R_2$, $R_3$, and $R_4$ may be a substituted or unsubstituted $C_6$ to $C_{30}$ aryl group.

In an implementation, in Formula 1, at least one of $R_1$, $R_2$, $R_3$, and $R_4$ may be a hydroxyl group-substituted $C_6$ to $C_{30}$ aryl group.

In an implementation, the phosphonium compound represented by Formula 1 may be represented by one of the following Formulae 1a to 1h.

[Formula 1a]
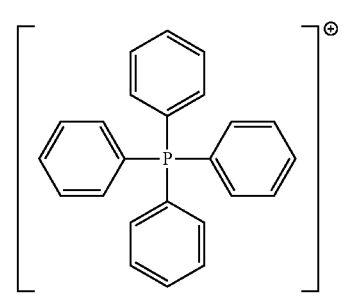

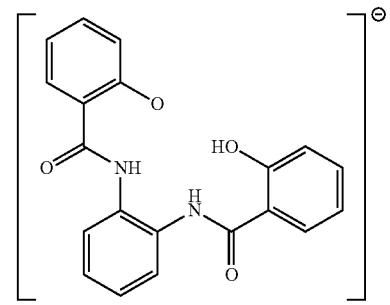

[Formula 1b]
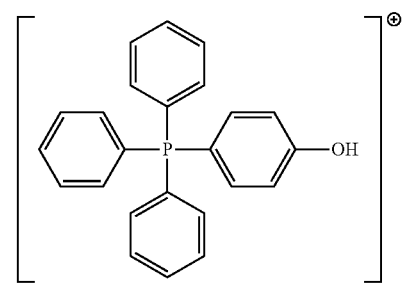

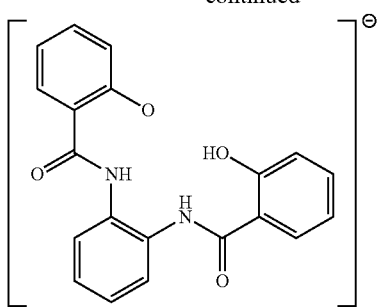
[Formula 1c]
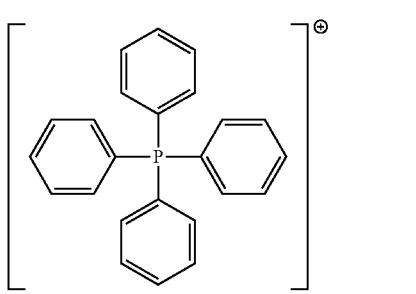
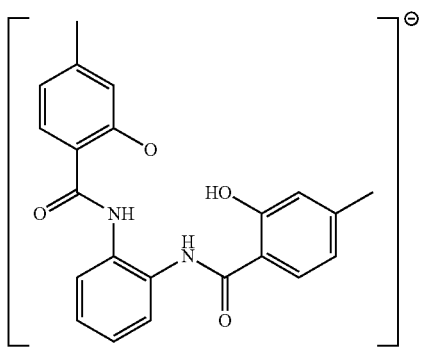
[Formula 1d]
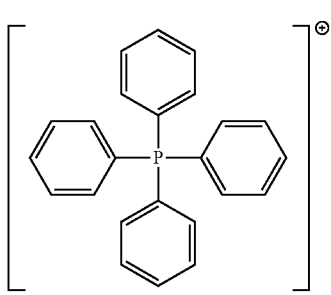
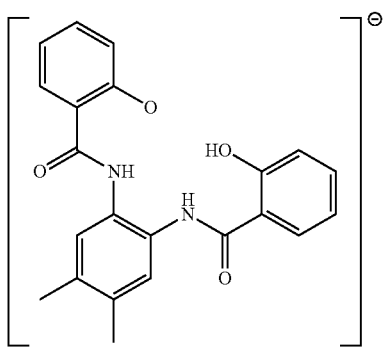
[Formula 1e]
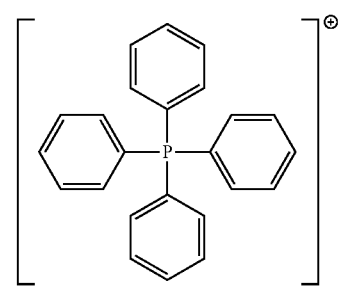
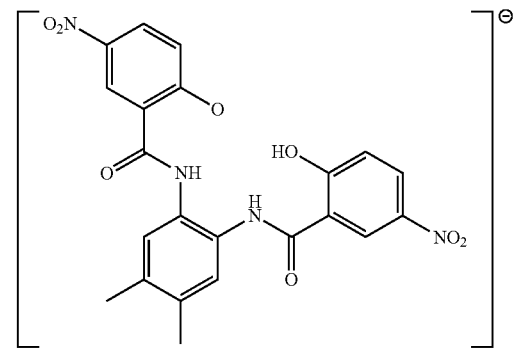
[Formula 1f]
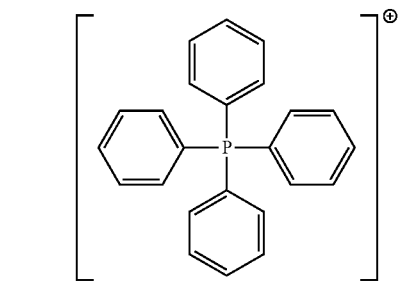
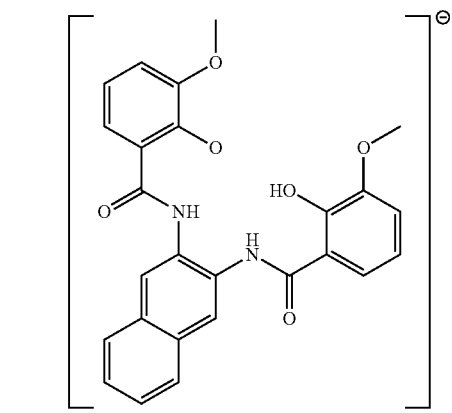
[Formula 1g]
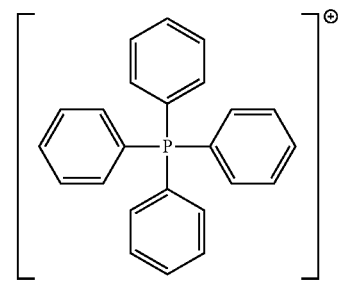

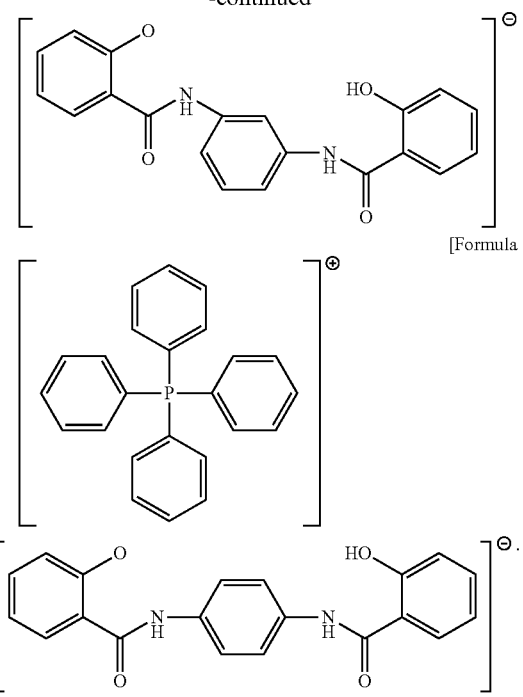

[Formula 1h]

In an implementation, the phosphonium compound may have a melting point of about 100° C. to about 130° C., e.g., 120° C. to 125° C. The phosphonium compound may be water-insoluble. Within this range, the phosphonium compound may be cured at low temperature.

The phosphonium compound may be added to a composition including at least one of an epoxy resin, a curing agent, and an inorganic filler so as to be used as a latent curing catalyst.

The phosphonium compound may help provide an epoxy resin composition that is capable of accelerating curing of an epoxy resin and a curing agent and that is capable of securing low temperature curability and high storage stability while minimizing viscosity change in a mixture including the epoxy resin, the curing agent, and the like within desired ranges of time and temperature. Storage stability refers to the ability to catalyze curing only at a desired curing temperature without any curing activity at temperature deviating from a desired curing temperature range. As a result, it is possible to store the epoxy resin composition for a long time without viscosity change. Generally, proceeding of curing reaction may cause increase in viscosity and deterioration in flowability when the epoxy resin composition is liquid, and may exhibit viscosity when the epoxy resin composition is solid.

The phosphonium compound may be prepared by, e.g., reacting a phosphonium cation-containing compound represented by Formula 2 with a phenylene-bis-benzamide anion-containing compound represented by Formula 3.

[Formula 2]

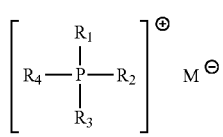

In Formula 2, $R_1$, $R_2$, $R_3$, and $R_4$ may each independently be or include, e.g., a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom. M may be, e.g., a halogen.

[Formula 3]

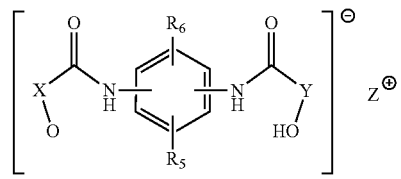

In Formula 3, X and Y may each independently be or include, e.g., a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ and $R_6$ are each independently hydrogen, a hydroxyl group, a $C_1$ to $C_{20}$ alkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group. Z may be, e.g., an alkali metal or Ag.

The halogen may include, e.g., fluorine, chlorine, bromine, or iodine. The alkali metal may include, e.g., lithium, sodium, potassium, rubidium, cesium, francium, or the like.

The phosphonium cation-containing compound may be prepared by, e.g., reacting a phosphine compound with an alkyl halide, an aryl halide, or an aralkyl halide in the presence of a solvent. The phosphonium cation-containing compound may be present in a phosphonium cation-containing salt. The phenylene-bis-benzamide anion-containing compound may be present in a phenylene-bis-benzamide anion-containing salt. Examples of the phosphine compound may include triphenylphosphine, methyldiphenylphosphine, dimethylphenylphosphine, ethyldiphenylphosphine, diphenylpropylphosphine, isopropyldiphenylphosphine, and diethylphenylphosphine.

The reaction between the compounds of Formulae 2 and 3 may be performed in an organic solvent, e.g., methanol, methylene chloride, acetonitrile, N,N-dimethylformamide, and toluene. The reaction may be performed by mixing the compounds of Formulae 2 and 3. Reaction between a phosphine compound and an alkyl halide, an aryl halide, or an aralkyl halide may produce the phosphonium cation-containing compound, which may be added to a phenylene-bis-benzamide anion-containing compound without an additional separation process.

In accordance with an embodiment, an epoxy resin composition may include, e.g., an epoxy resin, a curing agent, inorganic fillers, and a curing catalyst.

Epoxy Resin

In an implementation, the epoxy resin may have two or more epoxy groups per molecule. Examples of epoxy resins may include bisphenol A type epoxy resins, bisphenol F type epoxy resins, phenol novolac type epoxy resins, tert-butyl catechol type epoxy resins, naphthalene type epoxy resins, glycidyl amine type epoxy resins, cresol novolac type epoxy resins, biphenyl type epoxy resins, linear aliphatic epoxy resins, cycloaliphatic epoxy resins, heterocyclic epoxy resins, spiro ring-containing epoxy resins, cyclohexane dimethanol type epoxy resins, trimethylol type epoxy resins, and halogenated epoxy resins. These epoxy resins may be used alone or in combination thereof. In an implementation, the epoxy resins may have two or more epoxy groups and one or more hydroxyl groups per molecule. In an implementation, the epoxy resins may include at least one of solid phase epoxy resins and liquid phase epoxy resins. In an implementation, the solid phase epoxy resin may be used.

In an implementation, the epoxy resin may be a biphenyl type epoxy resin represented by Formula 4 or a phenol aralkyl type epoxy resin represented by Formula 5.

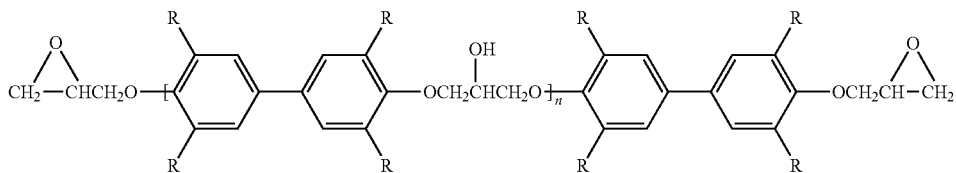

[Formula 4]

(In Formula 4, each R may independently be, e.g., a $C_1$ to $C_4$ alkyl group, and n may be, e.g., 0 to 7 on average.)

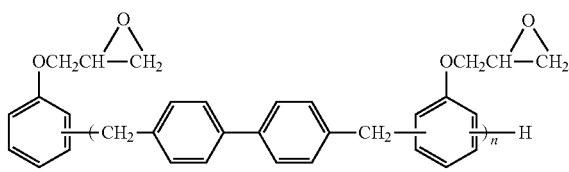

[Formula 5]

(In Formula 5, n may be, e.g., 1 to 7 on average.)

In an implementation, the composition may include the epoxy resin in an amount of about 2 wt % to about 17 wt %, e.g., about 3 wt % to about 15 wt % or about 3 wt % to about 12 wt % in terms of solid content (e.g., based on a total weight of the composition). Within this range, the composition may help secure curability.

Curing Agent

The curing agent may include, e.g., phenolaralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins synthesized from bisphenol A and resol, polyhydric phenol compounds (e.g., tris(hydroxyphenyl)methane and dihydroxybiphenyl), acid anhydrides (e.g., maleic anhydride and phthalic anhydride), aromatic amines (e.g., meta-phenylenediamine, diaminodiphenylmethane, and diaminodiphenylsulfone), or the like. In an implementation, the curing agent may include, e.g., a phenol resin having one or more hydroxyl groups.

In an implementation, the curing agent may be, e.g., a xyloc type phenol resin represented by Formula 6 or a phenolaralkyl type phenol resin represented by Formula 7.

In an implementation, the curing agent may be present in the epoxy resin composition in an amount of about 0.5 wt % to about 13 wt %, e.g., about 1 wt % to about 10 wt % or about 2 wt % to about 8 wt % in terms of solid content. Within this range, the epoxy resin composition can secure curability.

Inorganic Filler

The epoxy resin composition may further include an inorganic filler. The inorganic filler may help improve mechanical properties of the epoxy resin composition while reducing stress in the epoxy resin composition. Examples of the inorganic filler may include fused silica, crystalline silica, calcium carbonate, magnesium carbonate, alumina, magnesia, clay, talc, calcium silicate, titanium oxide, antimony oxide, and glass fibers.

In an implementation, fused silica having a low coefficient of linear expansion may be used, in view of stress reduction. The fused silica refers to amorphous silica having a specific gravity of 2.3 or less. The fused silica may be prepared by melting crystalline silica or may include amorphous silica products synthesized from various raw materials. In an implementation, the inorganic filler may include about 40 wt % to about 100 wt % of a fused silica mixture, based on the total weight of the inorganic fillers, wherein the fused silica mixture includes about 50 wt % to about 99 wt % of spherical fused silica having an average particle diameter of about 5 μm to about 30 μm and about 1 wt % to about 50 wt % of spherical fused silica having an average particle diameter of about 0.001 μm to about 1 μm. In an implementation, the inorganic filler may be adjusted to a maximum particle diameter of about 45 μm, about 55 μm or about 75 μm, depending upon application of the epoxy resin composition. Although the spherical fused silica may include conductive carbon as a foreign substance on the

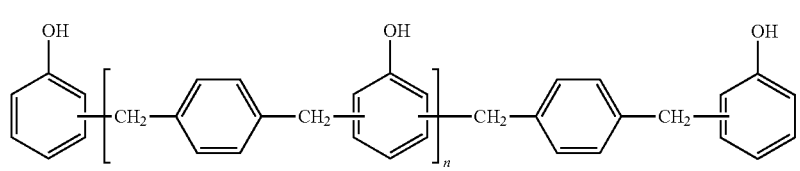

[Formula 6]

In Formula 6, n may be, e.g., 0 to 7 on average.

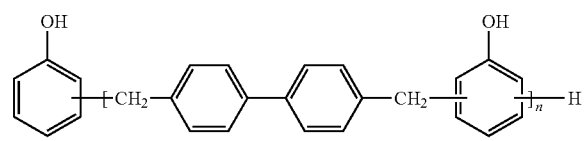

[Formula 7]

In Formula 7, n may be, e.g., 1 to 7 on average.

surface of silica, the spherical fused silica may incorporate a smaller amount of polar foreign substances.

The inorganic filler may be present in an appropriate amount depending upon desired physical properties of the epoxy resin composition, e.g., moldability, low-stress properties, and high-temperature strength. In an implementation, the inorganic filler may be present in an amount of about 70 wt % to about 95 wt %, e.g., about 75 wt % to about 92 wt %, in the epoxy resin composition (e.g., in terms of solid content). Within this range, the epoxy resin composition may help secure good flame retardancy, flowability, and reliability.

Curing Catalyst

The epoxy resin composition may include a curing catalyst including the phosphonium compound represented by Formula 1. In an implementation, the phosphonium compound may be present in the epoxy resin composition in an amount of about 0.01 wt % to about 5 wt %, e.g., about 0.02 wt % to about 1.5 wt % or about 0.05 wt % to about 1.5 wt %, in terms of solid content. Within this range, the epoxy resin composition may help secure flowability without delaying time for curing reaction.

In an implementation, the epoxy resin composition may further include a non-phosphonium curing catalyst (which does not contain phosphonium). Examples of non-phosphonium curing catalysts may include tertiary amines, organometallic compounds, organophosphorus compounds, imidazole, boron compounds, and the like. Examples of tertiary amines may include benzyldimethylamine, triethanolamine, triethylenediamine, diethylaminoethanol, tri(dimethylaminomethyl)phenol, 2,2-(dimethylaminomethyl)phenol, 2,4,6-tris(diaminomethyl)phenol, tri-2-ethyl hexanoate, and the like. Examples of organometallic compounds include chromium acetylacetonate, zinc acetylacetonate, nickel acetylacetonate, and the like. Examples of organophosphorus compounds may include tris-4-methoxyphosphine, triphenylphosphine, triphenylphosphinetriphenylborane, triphenylphosphine-1,4-benzoquinone adducts, and the like. Examples of imidazoles may include 2-methylimidazole, 2-phenylimidazole, 2-aminoimidazole, 2-methyl-1-vinylimidazole, 2-ethyl-4-methylimidazole, 2-heptadecyl imidazole, and the like. Examples of boron compounds may include triphenylphosphine tetraphenyl borate, tetraphenyl borate, trifluoroborane-n-hexylamine, trifluoroborane monoethylamine, tetrafluoroborane triethylamine, tetrafluoroboraneamine, and the like. In addition, it is possible to use 1,5-diazabicyclo[4.3.0]non-5-ene (DBN), 1,8-diazabicyclo [5.4.0]undec-7-ene (DBU), and a phenol novolac resin salt. In an implementation, the organophosphorus compounds, the boron compounds, and the amines or imidazole curing accelerators may be used alone or in combination. Adducts obtained by pre-reacting an epoxy resin or a curing agent may be used as the curing catalyst.

In an implementation, the phosphonium compound according to an embodiment may be present in an amount of about 10 wt % to about 100 wt %, e.g., about 60 wt % to about 100 wt %, in the curing catalyst (e.g., based on a total weight of the curing catalyst). Within this range, the epoxy resin composition may help secure flowability without delaying time for curing reaction.

In an implementation, the curing catalyst may be present in the epoxy resin composition in an amount of about 0.01 wt % to about 5 wt %, e.g., about 0.02 wt % to about 1.5 wt % or about 0.05 wt % to about 1.5 wt %, in terms of solid content. Within this range, the epoxy resin composition may help secure flowability without delaying time for curing reaction.

In an implementation, the composition may further include a suitable additive. In an implementation, the additive may include, e.g., a coupling agent, a release agent, a stress reliever, a crosslinking enhancer, a leveling agent, and/or a coloring agent.

In an implementation, the coupling agent may include, e.g., epoxysilane, aminosilane, mercaptosilane, alkylsilane, or alkoxysilane. In an implementation, the coupling agent may be present in an amount of about 0.1 wt % to about 1 wt % in the epoxy resin composition.

In an implementation, the release agent may include, e.g., paraffin wax, ester wax, higher fatty acids, metal salts of higher fatty acids, natural fatty acids, or natural fatty acid metal salts. In an implementation, the release agent may be present in an amount of about 0.1 wt % to about 1 wt % in the epoxy resin composition.

In an implementation, the stress reliever may include, e.g., modified silicone oil, silicone elastomers, silicone powder, or silicone resin. In an implementation, the stress reliever may be optionally present in an amount of about 6.5 wt % or less, e.g., about 1 wt % or less or about 0.1 wt % to about 1 wt % in the epoxy resin composition. As the modified silicone oil, a suitable silicone polymers having good heat resistance may be used. The modified silicone oil may include about 0.05 wt % to about 1.5 wt % of a silicone oil mixture based on the total weight of the epoxy resin composition, wherein the mixture may include, e.g., silicone oil having an epoxy functional group, silicone oil having an amine functional group, silicone oil having a carboxyl functional group, and a combination thereof. If the amount of the silicone oil is greater than 1.5 wt %, surface contamination may occur easily and lengthy resin bleed may be encountered. If the amount of the silicone oil is less than 0.05 wt %, sufficiently low modulus of elasticity may not be obtained. In addition, silicone powder having a median particle diameter of about 15 μm or less may be used in that the powder does not deteriorate moldability. In an implementation, the silicone powder may be present in an amount of about 5 wt % or less, e.g., about 0.1 wt % to about 5 wt %, based on the total weight of the epoxy resin composition.

In an implementation, the additive may be present in an amount of about 0.1 wt % to about 10 wt %, e.g., about 0.1 wt % to about 3 wt %, in the epoxy resin composition.

The epoxy resin composition may be curable at low temperature. For example, a curing initiation temperature may be about 90° C. to about 120° C. Within this range, the epoxy resin composition may be sufficiently cured at low temperature, thereby securing curing at low temperature.

In an implementation, the epoxy resin composition may have a flow length of about 59 inches to about 78 inches, e.g., about 71 inches to about 78 inches, as measured using a transfer molding press at 175° C. under a load of 70 kgf/cm² in accordance with EMMI-1-66. Within this range, the epoxy resin composition may be used for desired applications.

In an implementation, the epoxy resin composition may have a curing shrinkage rate of less than about 0.40%, e.g., less than about 0.33% or about 0.01% to about 0.32%, as calculated according to Equation 1. Within this range, the curing shrinkage rate is low, and the epoxy resin composition thus can be used for desired applications.

$$\text{Curing shrinkage} = (|C-D|/C) \times 100 \qquad \text{<Equation 1>}$$

In Equation 1, C is a length of a specimen obtained by transfer molding of the epoxy resin composition at 175° C. under a load of 70 kgf/cm², and D is a length of the specimen after post-curing the specimen at 170° C. to 180° C. for 4 hours and cooling.

In an implementation, the epoxy resin composition may have a storage stability of about 85% or more, e.g., about 90% or more or about 92% or more, as calculated according to Equation 2.

$$\text{Storage stability} = (F1/F0) \times 100 \qquad \text{<Equation 2>}$$

In Equation 2, F1 is a flow length (in inches) of the epoxy resin composition measured after storing the composition at 25° C./50% RH for 72 hours using a transfer molding press at 175° C. and 70 kgf/cm² in accordance with EMMI-1-66, and F0 is an initial flow length (in inches) of the epoxy resin composition.

In the epoxy resin composition, the epoxy resin may be used alone or in the form of adducts, such as a melt master batch, obtained by pre-reacting the epoxy resin with an additive, such as a curing agent, a curing catalyst, a release agent, a coupling agent, and a stress reliever. Although there is no particular restriction as to the method of preparing the epoxy resin composition according to an embodiment, the epoxy resin composition may be prepared by uniformly mixing all components of the resin composition using a suitable mixer, such as a Henschel mixer or a Lödige mixer, followed by melt-kneading in a roll mill or a kneader at about 90° C. to about 120° C., cooling, and pulverizing.

The epoxy resin composition according to an embodiment may be used in a broad range of applications requiring such an epoxy resin composition, e.g., in encapsulation of semiconductor devices, adhesive films, insulating resin sheets such as prepregs and the like, circuit boards, solder resists, underfills, die bonding materials, and component replenishing resins.

Encapsulation of Semiconductor Device

The epoxy resin composition may be used to encapsulate a semiconductor device and may include an epoxy resin, a curing agent, a phosphonium compound-containing curing catalyst, inorganic fillers, and additives.

A semiconductor device according to an embodiment may be encapsulated with the epoxy resin composition as set forth above.

FIG. 1 illustrates a cross-sectional view of a semiconductor device according to one embodiment. Referring to FIG. 1, a semiconductor device 100 according to this embodiment may include, e.g., a wiring board 10, bumps 30 on the wiring board 10, and a semiconductor chip 20 on the bumps 30. A gap between the wiring board 10 and the semiconductor chip 20 may be encapsulated with an epoxy resin composition 40. The epoxy resin composition may be an epoxy resin composition according to an embodiment.

Figure 2:
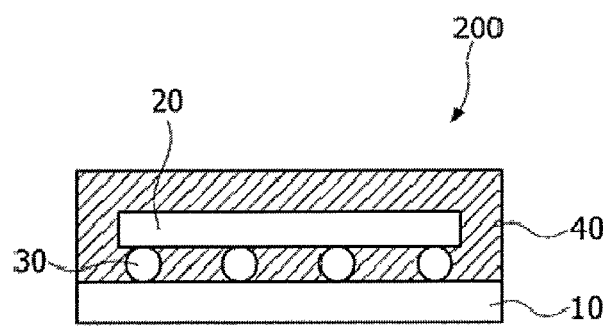
FIG. 2 illustrates a cross-sectional view of a semiconductor device according to another embodiment.

FIG. 2 illustrates a cross-sectional view of a semiconductor device according to another embodiment. Referring to FIG. 2, a semiconductor device 200 according to this embodiment may include a wiring board 10, bumps 30 on the wiring board 10, and a semiconductor chip 20 on the bumps 30. A gap between the wiring board 10 and the semiconductor chip 20 and an entirety of a top surface of the semiconductor chip 20 may be encapsulated with an epoxy resin composition 40. The epoxy resin composition may be an epoxy resin composition according to an embodiment.

Figure 3:
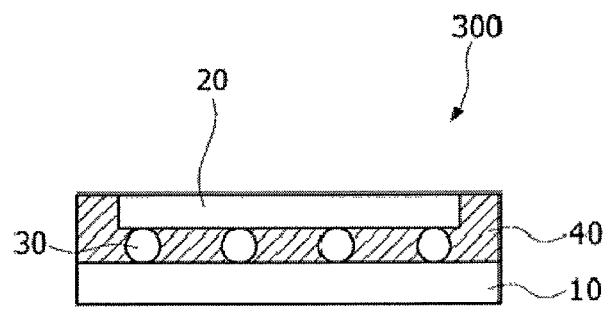
FIG. 3 illustrates a cross-sectional view of a semiconductor device according to a further embodiment.

FIG. 3 illustrates a cross-sectional view of a semiconductor device according to a further embodiment. Referring to FIG. 3, a semiconductor device 300 according to this embodiment may include a wiring board 10, bumps 30 on the wiring board 10, and a semiconductor chip 20 on the bumps 30. A gap between the wiring board 10 and the semiconductor chip 20 and an entirety of a side surface of the semiconductor chip 20 (e.g., except for the top surface) may be encapsulated with an epoxy resin composition 40. The epoxy resin composition may be an epoxy resin composition according to an embodiment.

In FIGS. 1 to 3, a size of each wiring board, bump and semiconductor chip, and the numbers of bumps may be modified.

In an implementation, the semiconductor device may be encapsulated with the epoxy resin composition by low-pressure transfer molding. In an implementation, the semiconductor device may also be molded by injection molding, casting, or the like. The semiconductor device that may be fabricated by such a molding process may include a copper lead frame, an iron lead frame, an iron lead frame pre-plated with at least one metal selected from the group consisting of nickel, copper, and palladium, or an organic laminate frame.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Preparative Example 1

Preparation of Compound Represented by Formula 1a 34.8 g of 1,2-phenylenebis(2-hydroxybenzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining 65 g of a compound. The compound was identified based on NMR data as a compound represented by Formula 1a (yield: 95%).

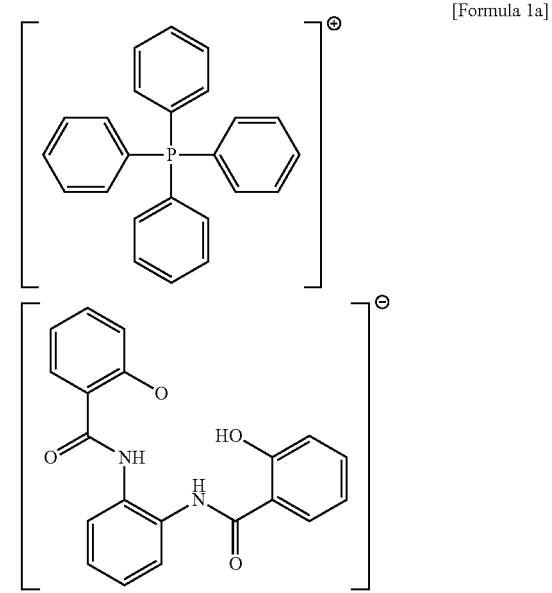

[Formula 1a]

$^1$H NMR (400 MHz, DMSO) 8.5 (br, 2H), 8.05-7.88 (m, 4H), 7.85-7.69 (m, 18H), 7.62 (m, 2), 7.34 (t, J=12.1 Hz, 2H), 7.01-6.98 (m, 4H), 6.91 (d, J=7.2 Hz, 2H), 4.9 (s, 1H) ppm; $^{13}$C NMR (100 MHz, DMSO) 164.8, 159.4, 137.4, 137.3, 133.6, 129.0, 128.9, 128.8, 128.2, 124.6 121.5, 119.9, 116.0 ppm; $^{31}$P NMR (166 MHz, DMSO) 24.20 ppm;

LC-MS m/z=686 (M⁺); Anal. Calcd for $C_{44}H_{35}N_2O_4P$: C, 76.95; H, 5.14; N, 4.08. Found: C, 76.49; H, 5.43; N, 4.38.

Preparative Example 2

Preparation of Compound Represented by Formula 1b 34.8 g of 1,2-phenylenebis(2-hydroxybenzamide) was added to 50 g of methanol (MeOH), followed by adding 21.6 g of 25% sodium methoxide solution, which in turn was completely dissolved while reacting at ambient temperature for 30 minutes. To the solution, a solution of 43 g of (4-hydroxy-phenyl)-triphenyl-phosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining 63 g of a compound. The compound was identified based on NMR data as a compound represented by Formula 1b (yield: 91%).

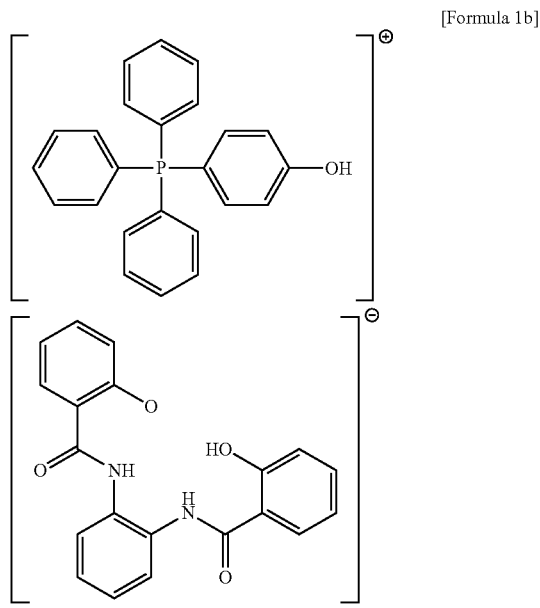

[Formula 1b]

1H NMR (400 MHz, DMSO) 8.5 (br, 2H), 7.94 (m, 3H), 7.82-7.66 (m, 14H), 7.62 (m, 2), 7.48-7.41 (m, 2H), 7.34 (t, J=12.1 Hz, 2H), 7.11-7.09 (m, 2H), 7.01-6.98 (m, 4H), 6.91 (d, J=7.2 Hz, 2H), 4.9 (s, 1H) ppm; $^{13}$C NMR (100 MHz, DMSO) 164.8, 159.4, 158.6, 137.7, 137.4, 137.3, 133.6, 130.0, 129.0, 128.9, 128.2, 128.1, 124.6, 121.5, 120.0, 119.9, 116.0, 115.9 ppm; $^{31}$P NMR (166 MHz, DMSO) 24.21 ppm; LC-MS m/z=702 (M⁺); Anal. Calcd for $C_{44}H_{35}N_2O_5P$: C, 75.20; H, 5.02; N, 3.99. Found: C, 75.41; H, 5.36; N, 4.14.

Preparative Example 3

Preparation of Compound Represented by Formula 1c 37.5 g of 1,2-phenylenebis(2-hydroxy-4-methyl-benzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining 65 g of a compound. The compound was identified based on NMR data as a compound represented by Formula 1c (yield: 92%).

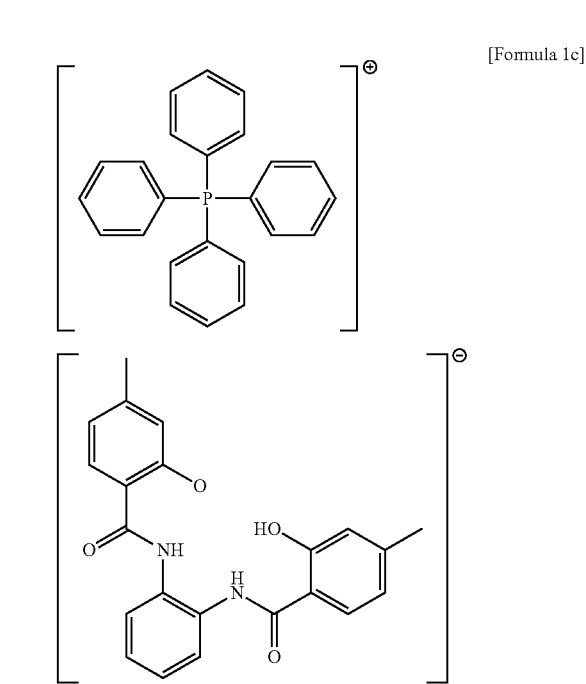

[Formula 1c]

$^1$H NMR (400 MHz, DMSO) 8.5 (br, 21-1), 8.05-7.88 (m, 4H), 7.85-7.69 (m, 18H), 7.62 (m, 2), 7.34 (d, J=2.8 Hz, 2H), 6.98 (m, 2H), 6.71 (s, 2H), 4.9 (s, 1H), 2.35 (s, 6H) ppm; $^{13}$C NMR (100 MHz, DMSO) 164.8, 159.3, 143.2, 137.3, 137.2, 129.0, 128.9, 128.8, 128.2, 128.0, 124.6 121.5, 116.9, 114.8, 24.6 ppm; $^{31}$P NMR (166 MHz, DMSO) 24.20 ppm; LC-MS m/z=714 (M⁺); Anal. Calcd for $C_{46}H_{39}N_2O_4P$: C, 77.29; H, 5.50; N, 3.92. Found: C, 77.14; H, 5.37; N, 3.99.

Preparative Example 4

Preparation of Compound Represented by Formula 1d 37.5 g of 4,5-dimethlyl-1,2-phenylenebis(2-hydroxybenzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining a compound. The compound was identified based on NMR data as a compound represented by Formula 1 d (yield: 92%).

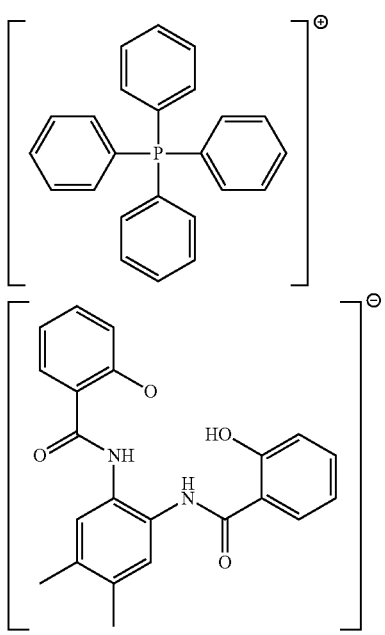

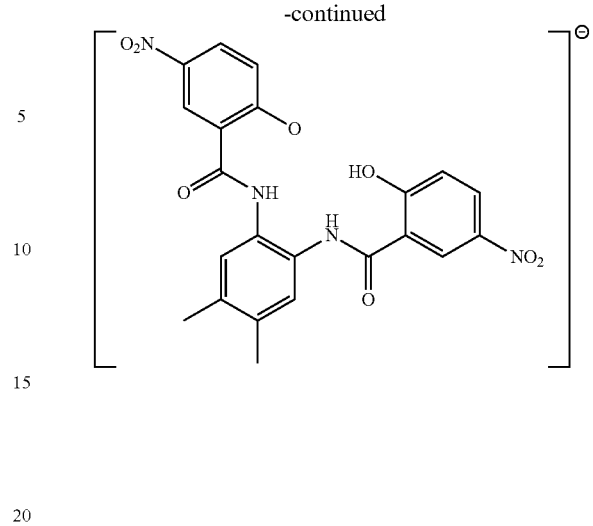

¹H NMR (400 MHz, DMSO) 8.5 (br, 2H), 8.05-7.88 (m, 4H), 7.85-7.69 (m, 18H), 7.34 (m, 2), 7.30 (s, 2H), 7.00 (m, 2H), 6.91 (d, J=2.8 Hz, 2H), 5.0 (s, 1H), 2.31 (s, 6H) ppm; ¹³C NMR (100 MHz, DMSO) 164.8, 159.4, 137.3, 137.2, 133.6, 132.7, 129.0, 128.9, 128.8, 125.1, 125.0, 121.5, 121.4, 119.9, 116.0, 17.8 ppm; ³¹P NMR (166 MHz, DMSO) 24.20 ppm; LC-MS m/z=714 (M⁺); Anal. Calcd for $C_{46}H_{39}N_2O_4P$: C, 77.29; H, 5.50; N, 3.92. Found: C, 77.21; H, 5.39; N, 3.53.

Preparative Example 5

Preparation of Compound Represented by Formula 1e 46.5 g of 4,5-dimethyl-1,2-phenylenebis(2-hydroxy-4-nitro-benzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining a compound. The compound was identified based on NMR data as a compound represented by Formula 1e (yield: 88%).

¹H NMR (400 MHz, DMSO) 8.71 (s, 2H), 8.5 (br, 2H), 8.27 (d, J=2.8 Hz, 2H), 8.05-7.88 (m, 4H), 7.85-7.69 (m, 16H), 7.30 (s, 2H), 7.17 (m, 2H), 4.8 (s, 1H), 2.35 (s, 6H) ppm; ¹³C NMR (100 MHz, DMSO) 165.5, 164.8, 141.1, 137.3, 137.2, 132.7, 128.9, 128.8, 125.9, 125.1, 123.8, 120.8, 116.9, 17.8 ppm; ³¹P NMR (166 MHz, DMSO) 24.20 ppm; LC-MS m/z=804 (M⁺); Anal. Calcd for $C_{46}H_{37}N_4O_8P$: C, 68.65; H, 4.63; N, 6.96. Found: C, 68.45; H, 4.37; N, 6.53.

Preparative Example 6

Preparation of Compound Represented by Formula 1f 45.7 g of 2,3-naphthalene-bis(2-hydroxy-3-methoxy-benzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining a compound. The compound was identified based on NMR data as a compound represented by Formula 1 f (yield: 91%).

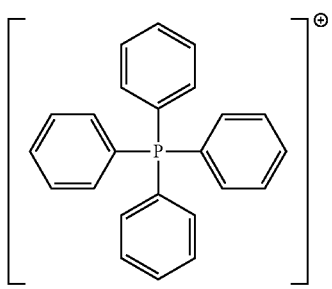

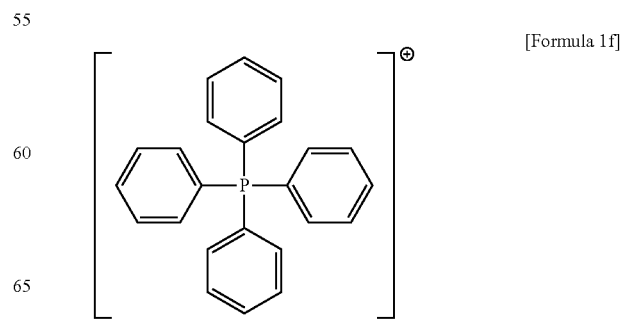

-continued

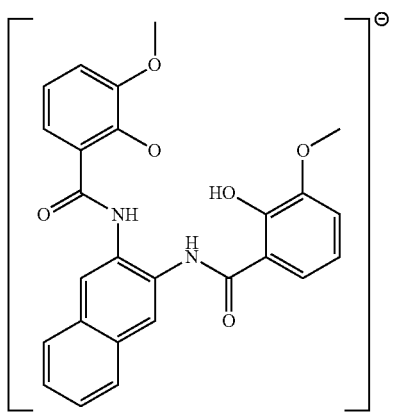

¹H NMR (400 MHz, DMSO) 8.5 (br, 2H), 8.05-7.88 (m, 4H), 7.85-7.69 (m, 16H), 7.34-7.32 (m, 4H), 7.00 (m, 2H), 6.89-6.85 (m, 4H), 6.63 (s, 2H), 5.0 (s, 1H), 3.73 (s, 6H) ppm; ¹³C NMR (100 MHz, DMSO) 164.8, 151.5, 148.4, 137.3, 137.2, 133.7, 128.9, 128.8, 126.7, 123.0, 122.6, 121.2, 120.9, 120.5, 119.1, 108.2, 56.2 ppm; ³¹P NMR (166 MHz, DMSO) 24.20 ppm; LC-MS m/z=796 (M⁺); Anal. Calcd for $C_{50}H_{41}N_2O_6P$: C, 75.36; H, 5.19; N, 3.52. Found: C, 75.44; H, 5.37; N, 3.53.

Preparative Example 7

Preparation of Compound Represented by Formula 1g 34.8 g of 1,3-phenylenebis(2-hydroxybenzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining 66 g of a compound. The compound was identified based on NMR data as a compound represented by Formula 1 g (yield: 96%).

[Formula 1g]

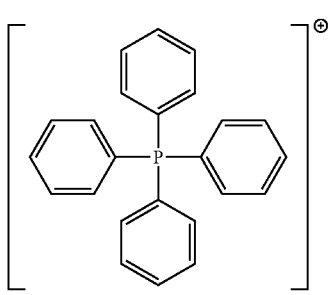

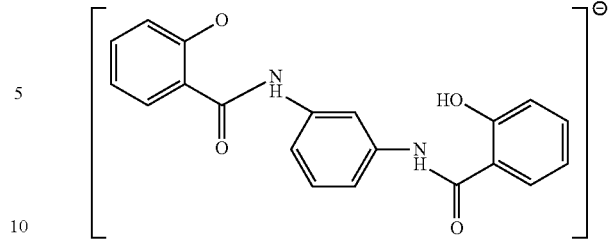

¹H NMR (400 MHz, DMSO) 8.5 (br, 2H), 8.05-7.88 (m, 5H), 7.85-7.69 (m, 18H), 7.38-7.34 (m, 4H), 7.22 (m, 1H), 7.0 (m, 2H), 6.91 (d, J=7.2 Hz, 2H), 5.0 (s, 1H) ppm; ¹³C NMR (100 MHz, DMSO) 164.8, 159.4, 137.3, 137.2, 136.1, 133.6, 128.9, 128.8, 121.5, 119.9, 117.2, 116.0, 113.3 ppm; ³¹P NMR (166 MHz, DMSO) 24.20 ppm; LC-MS m/z=686 (M⁺); Anal. Calcd for $C_{44}H_{35}N_2O_4P$: C, 76.95; H, 5.14; N, 4.08. Found: C, 76.76; H, 5.22; N, 4.30.

Preparative Example 8

Preparation of Compound Represented by Formula 1h 34.8 g of 1,4-phenylenebis(2-hydroxybenzamide) was added to 50 g of methanol (MeOH), followed by adding 21.6 g of 25% sodium methoxide solution, which in turn was completely dissolved while reacting at ambient temperature for 30 minutes. To the solution, a solution of 41 g of tetraphenylphosphonium bromide (previously dissolved in 50 g of methanol (MeOH)) was slowly added and the mixture was allowed to further react for 1 hour. The resulting white solid was filtered to remove a solvent component of the solution at low pressure, thereby obtaining 65 g of a compound. The compound was identified based on NMR data as a compound represented by Formula 1h (yield: 95%).

[Formula 1h]

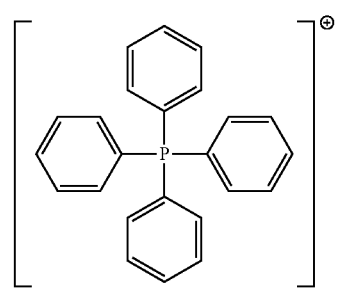

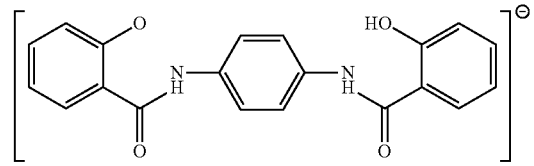

¹H NMR (400 MHz, DMSO) 8.5 (br, 2H), 8.05-7.88 (m, 4H), 7.85-7.69 (m, 22H), 7.34 (m, 2H), 7.0 (m, 2H), 6.91 (d, J=7.2 Hz, 2H), 5.0 (s, 1H) ppm; ¹³C NMR (100 MHz, DMSO) 164.8, 159.4, 137.3, 137.2, 133.6, 131.5, 128.9, 128.8, 121.8, 121.5, 119.9, 116.0 ppm; ³¹P NMR (166 MHz, DMSO) 24.20 ppm; LC-MS m/z=686 (M⁺); Anal. Calcd for $C_{44}H_{35}N_2O_4P$: C, 76.95; H, 5.14; N, 4.08. Found: C, 76.56; H, 5.23; N, 4.44.

Details of the components used in Examples and Comparative Examples are as follows.

(A) Epoxy Resin

NC-3000 (produced by Nippon Kayaku), a biphenyl type epoxy resin, was used.

(B) Curing Agent

HE100C-10 (produced by Air Water), a xyloc type phenol resin, was used.

(C) Curing Catalyst

Compounds (represented by Formulae 1a to 1h) prepared in Preparative Examples 1 to 8 were used as (C1) to (C8), respectively.

(C9) A compound represented by Formula 8 was used.

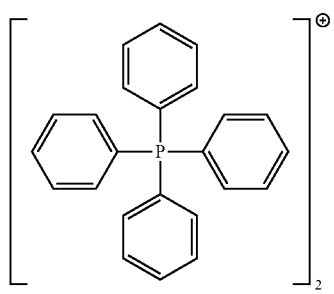

[Formula 8]

(C10)

Triphenyl phosphine was used (C11)

An adduct of triphenyl phosphine and 1,4-benzoquinone was used (D) Inorganic Filler A mixture of spherical fused silica having an average particle diameter of 18 m and spherical fused silica having an average particle diameter of 0.5 μm (in a weight ratio of 9:1) was used.

(E) Coupling Agent

A mixture of (e1) mercaptopropyl trimethoxy silane, KBM-803 (produced by Shin-etsu Co., Ltd.) and (e2) methyl trimethoxy silane, SZ-6070 (produced by Dow Corning Chemical Co., Ltd.) was used.

(F) Additive (f1) Carnauba wax as a mold release agent, and (f2) Carbon black, MA-600 (produced by Matsushita Chemical Co., Ltd.) as a coloring agent, were used.

Examples and Comparative Examples

The components were weighed as listed in Table 1 (unit: parts by weight) and uniformly mixed using a Henschel mixer to prepare first powder compositions. Then, each of the compositions was melt-kneaded by a continuous kneader at 95° C., cooled, and pulverized to prepare an epoxy resin composition for encapsulation of a semiconductor device.

TABLE 1

| | | Example | | | | | | | | Comparative Example | | |
|---|---|---|---|---|---|---|---|---|---|---|---|---|
| | | 1 | 2 | 3 | 4 | 5 | 6 | 7 | 8 | 1 | 2 | 3 |
| (A) | | 8.5 | 8.5 | 8.5 | 8.5 | 8.5 | 8.5 | 8.5 | 8.5 | 8.5 | 8.5 | 8.5 |
| (B) | | 5.2 | 5.2 | 5.2 | 5.2 | 5.2 | 5.2 | 5.2 | 5.2 | 5.2 | 5.2 | 5.2 |
| (C) | C1 | 0.3 | — | — | — | — | — | — | — | — | — | — |
| | C2 | — | 0.3 | — | — | — | — | — | — | — | — | — |
| | C3 | — | — | 0.3 | — | — | — | — | — | — | — | — |
| | C4 | — | — | — | 0.3 | — | — | — | — | — | — | — |
| | C5 | — | — | — | — | 0.3 | — | — | — | — | — | — |
| | C6 | — | — | — | — | — | 0.3 | — | — | — | — | — |
| | C7 | — | — | — | — | — | — | 0.3 | — | — | — | — |
| | C8 | — | — | — | — | — | — | — | 0.3 | — | — | — |
| | C9 | — | — | — | — | — | — | — | — | 0.3 | — | — |
| | C10 | — | — | — | — | — | — | — | — | — | 0.3 | — |
| | C11 | — | — | — | — | — | — | — | — | — | — | 0.3 |
| (D) | | 85 | 85 | 85 | 85 | 85 | 85 | 85 | 85 | 85 | 85 | 85 |
| (E) | (e1) | 0.2 | 0.2 | 0.2 | 0.2 | 0.2 | 0.2 | 0.2 | 0.2 | 0.2 | 0.2 | 0.2 |
| | (e2) | 0.2 | 0.2 | 0.2 | 0.2 | 0.2 | 0.2 | 0.2 | 0.2 | 0.2 | 0.2 | 0.2 |
| (F) | (f1) | 0.3 | 0.3 | 0.3 | 0.3 | 0.3 | 0.3 | 0.3 | 0.3 | 0.3 | 0.3 | 0.3 |
| | (f2) | 0.3 | 0.3 | 0.3 | 0.3 | 0.3 | 0.3 | 0.3 | 0.3 | 0.3 | 0.3 | 0.3 |
| Total | | 100 | 100 | 100 | 100 | 100 | 100 | 100 | 100 | 100 | 100 | 100 |

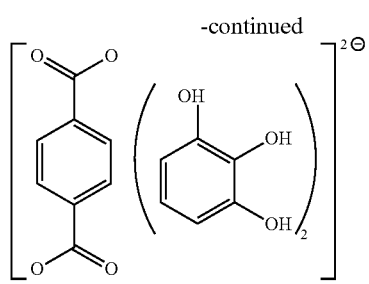

-continued (1) Flowability (inches): The flow length of each of the epoxy resin compositions was measured using a transfer molding press in a test mold at 175° C. under a load of 70 kgf/cm$^2$ in accordance with EMMI-1-66. EMMI-1-66 is a method of evaluating the molding flow of a resin to injection or transfer molding in which the melt is injected into a spiral runner of constant trapezoidal cross section with numbered and subdivided centimeters marked along the runner. The mold is filled from a sprue at the center of the spiral and pressure is maintained until flow stops, the number just aft of the molded-spiral tip giving the flow distance. A higher measured value indicates better flowability.

(2) Curing shrinkage (%): Each of the epoxy resin compositions was molded using a transfer molding press in an ASTM mold for flexural strength specimen construction at 175° C. and 70 kgf/cm² to obtain a molded specimen (125×12.6×6.4 mm). The specimen was subjected to post-molding curing (PMC) in an oven at 170° C. to 180° C. for 4 hours. After cooling, the length of the specimen was measured using calipers. Curing shrinkage of the epoxy resin composition was calculated according to the following Equation 1.

Curing shrinkage=(|C−D|/C)×100

In Equation 1, C is the length of the specimen obtained by transfer molding of the epoxy resin composition at 175° C. under a load of 70 kgf/cm², and D is the length of the specimen after post-curing the specimen at 170° C. to 180° C. for 4 hours and cooling.

(3) Glass transition temperature (° C.): Glass transition temperature of each of the epoxy resin compositions prepared in the Examples and Comparative Examples was measured using a thermomechanical analyzer (TMA). Here, the TMA was set to heat the resin composition at a rate of 10° C./min from 25° C. to 300° C.

(4) Moisture absorption (%): Each of the resin compositions prepared in the Examples and Comparative Examples was molded at a mold temperature of 170° C. to 180° C., a clamp pressure of 70 kg/cm², a transfer pressure of 1,000 psi and a transfer speed of 0.5 cm/s to 1 cm/s for a curing time of 120 sec to obtain a cured specimen in the form of a disc having a diameter of 50 mm and a thickness of 1.0 mm. The specimen was subjected to post-molding curing (PMC) in an oven at 170° C. to 180° C. for 4 hours and allowed to stand at 85° C. and 85% RH for 168 hours. The weights of the specimen before and after moisture absorption were measured. Moisture absorption of the resin composition was calculated according to the following Equation 3.

Moisture absorption (%)=[(Weight of the specimen after moisture absorption−Weight of the specimen before moisture absorption)÷(Weight of the specimen before moisture absorption)]×100

(5) Adhesive strength (kgf): A copper metal device having a size adapted to a mold for adhesive strength measurement was prepared as a test piece. Each of the resin compositions prepared in the Examples and Comparative Examples was molded on the test piece at a mold temperature of 170° C. to 180° C., a clamp pressure of 70 kgf/cm², a transfer pressure of 1,000 psi, and a transfer speed of 0.5 cm/s to 1 cm/s for a curing time of 120 sec to obtain a cured specimen. The specimen was subjected to post-molding curing (PMC) in an oven at 170° C. to 180° C. for 4 hours. The area of the epoxy resin composition in contact with the specimen was 40±1 mm². The adhesive strength of the epoxy resin composition was measured using a universal testing machine (UTM). 12 specimens of each composition were produced. After the measurement procedure was repeated, the measured adhesive strength values were averaged.

(6) Degree of cure (Shore-D): Each of the epoxy resin compositions was cured using a multi-plunger system (MPS) equipped with a mold at 175° C. for 50 sec, 60 sec, 70 sec, 80 sec, and 90 sec to construct exposed thin quad flat packages (eTQFPs), each including a copper metal device having a width of 24 mm, a length of 24 mm and a thickness of 1 mm. The hardness values of the cured products in the packages on the mold according to the curing periods of time were directly measured using a Shore D durometer. A higher hardness value indicates better degree of cure.

(7) Storage stability (%): The flow length (in inches) of each of the epoxy resin compositions was measured in accordance with the method described in (1) while storing the compositions for 3 days in a thermo-hygrostat set to 25° C./50% RH and measuring every 24 hours. Percent (%) of the flow length after storage to the flow length immediately after preparation of the composition was calculated. A higher value indicates better storage stability. Storage stability after 72 hours of the epoxy resin composition was calculated according to the following Equation 2.

Storage stability=(F1/F0)×100

(wherein F1 is the flow length (in inches) of the epoxy resin composition measured after storing the composition at 25° C./50% RH for 72 hours using a transfer molding press at 175° C. and 70 kgf/cm² in accordance with EMMI-1-66, and F0 is the initial flow length (in inches) of the epoxy resin composition.)

(8) Reliability: Each of the eTQFP packages for the evaluation of flexural properties was dried at 125° C. for 24 h. After 5 cycles of thermal shock testing (1 cycle refers to a series of exposures of the package to −65° C. for 10 min, 25° C. for 10 min, and 150° C. for 10 min), the package was allowed to stand at 85° C. and 60% RH for 168 hours and treated by IR reflow three times at 260° C. for 30 sec (preconditioning). After preconditioning, the occurrence of external cracks in the package was observed using an optical microscope, and the occurrence of peeling between the epoxy resin composition and a lead frame was evaluated by scanning acoustic microscopy (C-SAM) as a non-destructive test method. External cracks of the package or peeling between the epoxy resin composition and the lead frame mean that reliability of the package cannot be guaranteed.

TABLE 2

| | | | Example | | | | | | | | Comparative Example | | |
|---|---|---|---|---|---|---|---|---|---|---|---|---|---|
| | Evaluation item | | 1 | 2 | 3 | 4 | 5 | 6 | 7 | 8 | 1 | 2 | 3 |
| Basic physical properties | Flowability (inch) | | 75 | 71 | 74 | 73 | 78 | 77 | 76 | 74 | 66 | 52 | 58 |
| | Curing shrinkage (%) | | 0.31 | 0.32 | 0.31 | 0.32 | 0.31 | 0.32 | 0.31 | 0.32 | 0.34 | 0.42 | 0.40 |
| | Glass transition temp. (° C.) | | 123 | 123 | 124 | 124 | 123 | 124 | 123 | 123 | 123 | 121 | 122 |
| | Moisture absorption (%) | | 0.25 | 0.25 | 0.24 | 0.24 | 0.25 | 0.24 | 0.25 | 0.25 | 0.24 | 0.25 | 0.26 |
| | Adhesive strength (kgf) | | 77 | 74 | 75 | 76 | 76 | 77 | 77 | 77 | 74 | 72 | 74 |
| Evaluation of packages | Degree of cure (Shore-D) according to curing time | 50 sec | 72 | 72 | 71 | 71 | 71 | 72 | 71 | 71 | 74 | 72 | 74 |
| | | 60 sec | 74 | 73 | 73 | 73 | 72 | 73 | 72 | 73 | 73 | 60 | 64 |
| | | 70 sec | 76 | 75 | 76 | 75 | 78 | 74 | 75 | 75 | 76 | 64 | 66 |
| | | 80 sec | 77 | 77 | 77 | 77 | 78 | 77 | 76 | 76 | 76 | 67 | 70 |
| | | 90 sec | 78 | 78 | 78 | 78 | 79 | 77 | 77 | 77 | 76 | 67 | 71 |

TABLE 2-continued

| Evaluation item | | Example | | | | | | | | Comparative Example | | |
|---|---|---|---|---|---|---|---|---|---|---|---|---|
| | | 1 | 2 | 3 | 4 | 5 | 6 | 7 | 8 | 1 | 2 | 3 |
| Storage stability | 24 hr (%) | 98 | 97 | 98 | 97 | 98 | 98 | 98 | 98 | 92 | 90 | 92 |
| | 48 hr (%) | 94 | 95 | 94 | 92 | 96 | 95 | 94 | 94 | 89 | 84 | 88 |
| | 72 hr (%) | 92 | 93 | 92 | 93 | 93 | 94 | 92 | 92 | 84 | 74 | 79 |
| Reliability | Number of packages suffering cracking | 0 | 0 | 0 | 0 | 0 | 0 | 0 | 0 | 0 | 0 | 0 |
| | Number of packages suffering peeling | 0 | 0 | 0 | 0 | 0 | 0 | 0 | 0 | 5 | 45 | 20 |
| | Number of tested semiconductors | 88 | 88 | 88 | 88 | 88 | 88 | 88 | 88 | 88 | 88 | 88 |

It may be seen that the epoxy resin compositions prepared in Examples 1 to 8 had higher flowability and higher degree of cure (even with shorter curing times) in view of curability for each curing period of time than the epoxy resin compositions of Comparative Examples. For storage stability, it may be that the epoxy resin compositions of Examples 1 to 8 showed less change in flowability after 72 hours of storage. Further, it may be seen that the epoxy resin compositions of Examples 1 to 8 did not suffer from cracking and thus had excellent crack resistance and did not suffer from peeling and thus had excellent moisture resistance reliability.

The compositions of Comparative Examples 1 to 3 (not including the phosphonium compound according to an embodiment) had low flowability and high curing shrinkage, had low curability for each curing period of time, and low storage stability when used in a package, and suffered from peeling and thus exhibited poor moisture resistance reliability. Therefore, it may be seen that the compositions of Comparative Examples 1 to 3 could not ensure desired effects.

By way of summation and review, with the trend toward compact, lightweight and high performance electronic devices, high integration of semiconductor devices has been accelerated year by year. Some issues may arise with increasing demand for surface mounting of semiconductor devices. Some desirable features of packaging materials for semiconductor devices may include rapid curability to improve productivity and storage stability to improve handling performance during distribution and storage.

The embodiments may provide a compound for curing catalysts having high storage stability, which is capable of accelerating curing of an epoxy resin and curing of an epoxy resin at low temperature while minimizing viscosity change in a mixture including the compound, an epoxy resin, a curing agent and the like even within desired ranges of time and temperature, thereby ensuring that the epoxy resin composition obtained after curing at high temperature does not exhibit any deterioration in moldability, mechanical, electrical, and chemical properties of molded products due to decrease in flowability; an epoxy resin composition including the same; and a semiconductor device encapsulated with the epoxy resin composition.

The embodiments may provide a compound for curing catalysts capable of accelerating curing of an epoxy resin, having good flowability upon molding and high curing strength, and capable of being rapidly cured.

The embodiments may provide a compound for curing catalysts capable of accelerating curing of an epoxy resin at low temperature.

The embodiments may provide a compound for curing catalysts having high storage stability, which can catalyze curing only at a desired curing temperature without exhibiting any curing activity at a temperature deviating from the desired curing temperature.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A phosphonium compound represented by Formula 1:

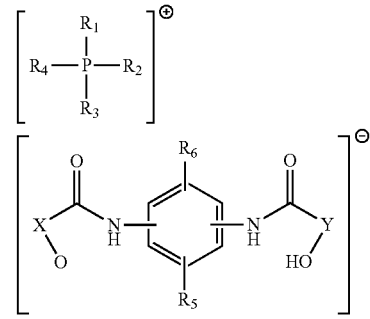

Formula 1 wherein:
$R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom;

X and Y are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group;

$R_5$ and $R_6$ are each independently hydrogen, a hydroxyl group, a $C_1$ to $C_{20}$ alkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group.

2. The phosphonium compound as claimed in claim 1, wherein $R_1$, $R_2$, $R_3$, and $R_4$ are each independently a substituted or unsubstituted $C_6$ to $C_{30}$ aryl group.

3. The phosphonium compound as claimed in claim 2, wherein at least one of $R_1$, $R_2$, $R_3$, and $R_4$ is a hydroxyl group-substituted $C_6$ to $C_{30}$ aryl group.

4. The phosphonium compound as claimed in claim 1, wherein the phosphonium compound is represented by one of the following Formulae 1a to 1h.

Formula 1a

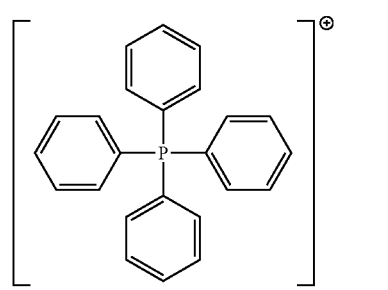

Formula 1b

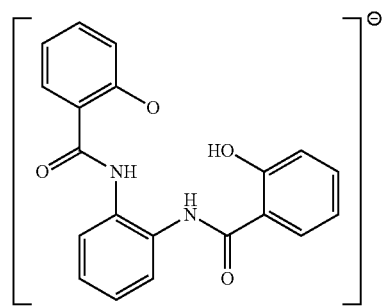

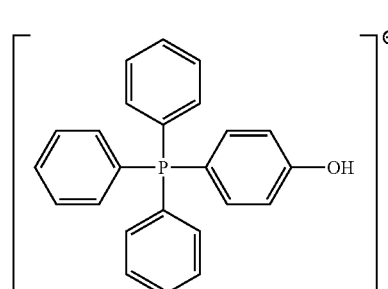

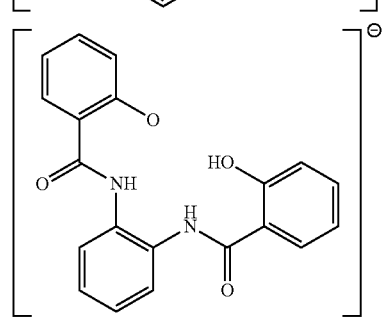

Formula 1c

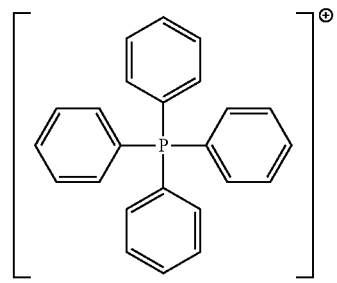

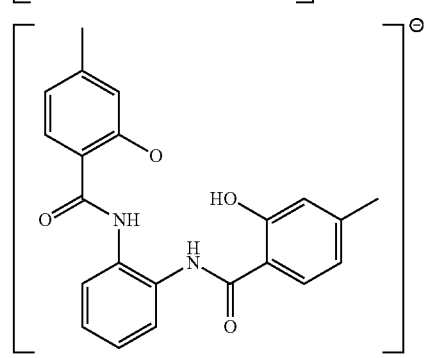

Formula 1d

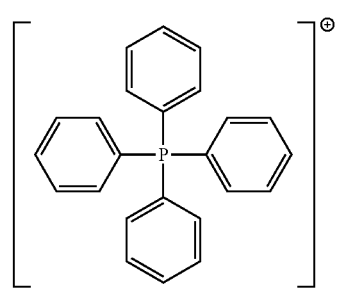

Formula 1e

-continued

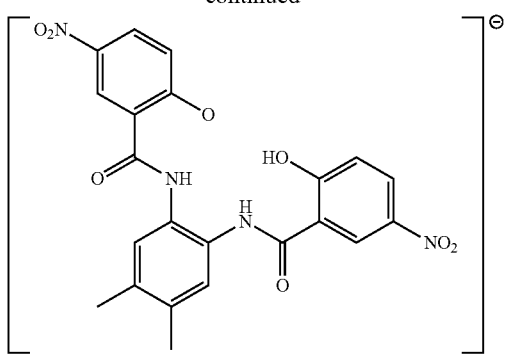

Formula 1f

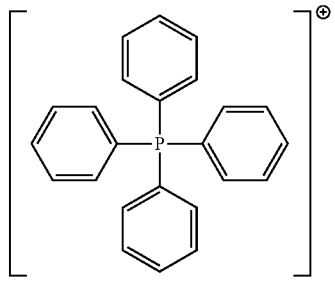

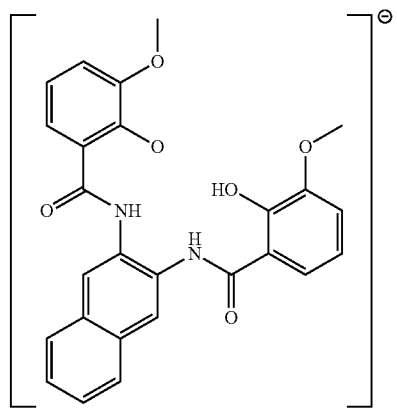

Formula 1g

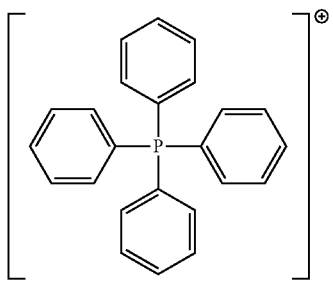

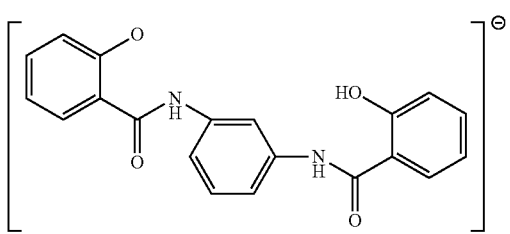

-continued

Formula 1h

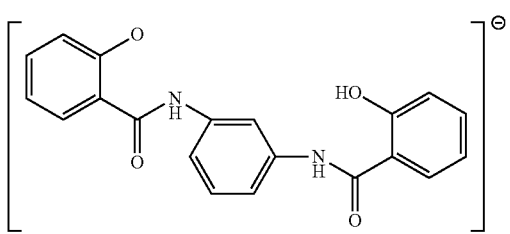

5. An epoxy resin composition, comprising:
an epoxy resin,
a curing agent,
an inorganic filler, and
a curing catalyst, wherein the curing catalyst includes the phosphonium compound as claimed in claim 1.

6. The epoxy resin composition as claimed in claim 5, wherein the epoxy resin includes at least one of a bisphenol A epoxy resin, a bisphenol F epoxy resin, a phenol novolac epoxy resin, a tert-butyl catechol epoxy resin, a naphthalene epoxy resin, a glycidylamine epoxy resin, a cresol novolac epoxy resin, a biphenyl epoxy resin, a linear aliphatic epoxy resin, a cycloaliphatic epoxy resin, a heterocyclic epoxy resin, a spiro ring-containing epoxy resin, a cyclohexane dimethanol epoxy resin, a trimethylol epoxy resin, and a halogenated epoxy resin.

7. The epoxy resin composition as claimed in claim 5, wherein the curing agent includes a phenol resin.

8. The epoxy resin composition as claimed in claim 5, wherein the curing agent includes at least one of a phenol aralkyl phenol resin, a phenol novolac phenol resin, a xyloc phenol resin, a cresol novolac phenol resin, a naphthol phenol resin, a terpene phenol resin, a polyfunctional phenol resin, a dicyclopentadiene-based phenol resin, a novolac phenol resin synthesized from bisphenol A and resorcinol, a polyhydric phenolic compound, an acid anhydride, and an aromatic amine.

9. The epoxy resin composition as claimed in claim 5, wherein the curing catalyst is present in the epoxy resin composition in an amount of about 0.01 wt % to about 5 wt %, in terms of solid content.

10. The epoxy resin composition as claimed in claim 5, wherein the phosphonium compound is present in the curing catalyst in an amount of about 10 wt % to about 100 wt %, based on a total weight of the curing catalyst.

11. The epoxy resin composition as claimed in claim 6, wherein the epoxy resin composition has a curing shrinkage rate of less than about 0.40%, as calculated according to Equation 1:

$$\text{Curing shrinkage} = (|C-D|/C) \times 100 \quad \text{Equation 1}$$

wherein, in Equation 1, C is a length of a specimen obtained by transfer molding the epoxy resin composition at 175° C. under a load of 70 kgf/cm², and D is a length of the specimen after post-curing the specimen at 170° C. to 180° C. for 4 hours and cooling.

12. The epoxy resin composition as claimed in claim 5, wherein the epoxy resin composition has a storage stability after 72 hours of about 85% or more, as calculated according to Equation 2:

Storage stability=$(F1/F0) \times 100$  Equation 2 wherein, in Equation 2, F1 is a flow length in inches of the epoxy resin composition, measured after storing the composition at 25° C./50% RH for 72 hours, using a transfer molding press at 175° C. and 70 kgf/cm² in accordance with EMMI-1-66, and F0 is an initial flow length in inches of the epoxy resin composition.

13. A semiconductor device encapsulated with the epoxy resin composition as claimed in claim 5.

14. A method of preparing a phosphonium compound, the method comprising reacting a phosphonium cation-containing compound represented by Formula 2 with a phenylene-bis-benzamide anion-containing compound represented by Formula 3:

Formula 2

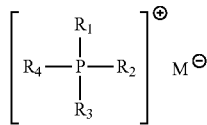

Formula 3

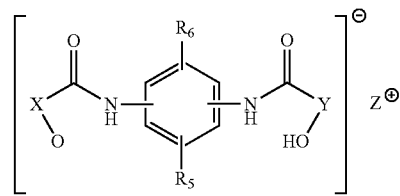

wherein, in Formula 2, $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom, and M is a halogen, and wherein, in Formula 3, X and Y are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ and $R_6$ are each independently hydrogen, a hydroxyl group, a $C_1$ to $C_{20}$ alkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group; and Z is an alkali metal or Ag.

\* \* \* \* \*